(12) United States Patent
Twigg

(10) Patent No.: US 10,006,847 B2
(45) Date of Patent: Jun. 26, 2018

(54) NANOPARTICLE COUNTING

(71) Applicant: Twigg Scientific & Technical LTD, Cambridgeshire (GB)

(72) Inventor: Martyn Vincent Twigg, Caxton (GB)

(73) Assignee: Twigg Scientific & Technical LTD, Cambridgeshire (GB)

( * ) Notice: Subject to any disclaimer, the term of this patent is extended or adjusted under 35 U.S.C. 154(b) by 90 days.

(21) Appl. No.: 15/024,286

(22) PCT Filed: Oct. 6, 2014

(86) PCT No.: PCT/GB2014/000397
§ 371 (c)(1),
(2) Date: Mar. 23, 2016

(87) PCT Pub. No.: WO2015/052463
PCT Pub. Date: Apr. 16, 2015

(65) Prior Publication Data
US 2016/0231221 A1    Aug. 11, 2016

(30) Foreign Application Priority Data
Oct. 8, 2013  (GB) ............................. GB1317744.9

(51) Int. Cl.
*G01N 15/06* (2006.01)
*F01N 3/022* (2006.01)
(Continued)

(52) U.S. Cl.
CPC ........... *G01N 15/065* (2013.01); *F01N 3/085* (2013.01); *F01N 3/0842* (2013.01); *F01N 3/281* (2013.01);
(Continued)

(58) Field of Classification Search
CPC .......... F01N 3/08; F01N 3/0842; F01N 3/085; F01N 3/022; F01N 3/28; F01N 3/281;
(Continued)

(56) References Cited

U.S. PATENT DOCUMENTS

| | | | |
|---|---|---|---|
| 6,288,008 B1 * | 9/2001 | Matsumoto | B01J 35/04 422/180 |
| 2004/0118747 A1 * | 6/2004 | Cutler | B01D 53/0415 208/208 R |

(Continued)

FOREIGN PATENT DOCUMENTS

| | | | |
|---|---|---|---|
| DE | 202013100053 | 3/2013 | |
| JP | 08206516 A * | 8/1996 | B01J 35/04 |

(Continued)

OTHER PUBLICATIONS

PCT/GB2014/000397, International Search Report and Written Opinion dated Apr. 16, 2015, 11 pgs.
(Continued)

*Primary Examiner* — Nguyen Ha
(74) *Attorney, Agent, or Firm* — Schwegman Lundberg & Woessner, P.A.

(57) ABSTRACT

An improved instrument for counting nanoparticles suspended in a gas, particularly in a combustion gas, incorporates a counter device such as a Condensation Particle Counter, incorporates a pre-treatment stage to remove substances which can cause nucleation and false results, comprising a flow through monolith carrying an oxidation catalyst and an absorber, wherein the monolith has a call density of no more than 400 cells per square inch and an open area of at least 80%.

12 Claims, 1 Drawing Sheet

(51) Int. Cl.
*F01N 3/035* (2006.01)
*F01N 3/08* (2006.01)
*F01N 3/28* (2006.01)
*G01N 33/00* (2006.01)
*G01N 1/34* (2006.01)
*G01N 15/00* (2006.01)

(52) U.S. Cl.
CPC ............. *F01N 3/2828* (2013.01); *G01N 1/34* (2013.01); *G01N 33/0013* (2013.01); *F01N 2560/05* (2013.01); *G01N 2015/0038* (2013.01)

(58) Field of Classification Search
CPC .... F01N 3/2828; F01N 3/035; F01N 2560/05; G01N 1/34; G01N 15/06; G01N 15/065; G01N 33/0013; G01N 2015/0038
See application file for complete search history.

(56) References Cited

U.S. PATENT DOCUMENTS

| | | | |
|---|---|---|---|
| 2004/0139785 A1 | 7/2004 | Abdul-Khalek | |
| 2007/0055438 A1* | 3/2007 | Twigg | F01N 3/035 701/109 |
| 2007/0089399 A1* | 4/2007 | Rhodes | F01N 3/027 60/278 |
| 2011/0150718 A1* | 6/2011 | Wieres | B01J 35/04 422/180 |
| 2014/0093435 A1 | 4/2014 | Giechaskiel et al. | |

FOREIGN PATENT DOCUMENTS

| | | |
|---|---|---|
| WO | WO-02/18753 A1 | 3/2002 |
| WO | WO-2004/046517 A2 | 6/2004 |
| WO | WO-2004/097400 A1 | 11/2004 |

OTHER PUBLICATIONS

Abdul-Khalek, I., et al., "Real Time Measurement of Volatile and Soiid Exhaust Particles Using a Catalytic Stripper", abstract oniy, SAE Technicai Paper 950236, 1995. Retrieved from the Internet: <URL: http://papers.sae.org/9503236/ >, 2 pgs.

Rongchai, J.K., et al., "High Temperature Condensation Particle Counter (HT—CPC)", Cambridge Particle Meeting, 2013. Retrieved from the Internet: < URL: http://www.cambridgeparticlemeeting.org/sites/default/files/Presentations/2013/NCoilings(Uo fCambridge)._2013_Hot%20condensation%20particle%20counter.pdf >, 20 pgs.

United Kingdom Application No. GB1317744.9, Search Report dated Apr. 3, 2014, 1 pg.

* cited by examiner

NANOPARTICLE COUNTING

This application is a U.S. National Stage Filing under 35 U.S.C. 371 from International Application No. PCT/GB2014/000397, filed on Oct. 6, 2014, and published as WO 2015/052463 A1 on Apr. 16, 2015, and which claims the benefit of priority to United Kingdom Patent Application No. 1317744.9, filed on Oct. 8, 2013, each of which is hereby incorporated by reference herein in its entirety.

The present invention concerns improvements in nanoparticle counting, and more particularly concerns the counting of solid particles in an atmosphere containing condensable hydrocarbons and sulphate type species.

It has become important for environmental and health reasons to count the number of nanoparticles (size less than 100 nm) in a gaseous atmosphere. Internal combustion engines in particular emit particles in addition to regulated gaseous pollutants such as NOx, CO, partially burnt and unburnt hydrocarbons (HC). Whilst large size carbonaceous particles formed the highly visible diesel "smoke" emitted by older design diesel engines, especially when the engine operated under load, modern high speed turbocharged, intercooled, diesel engines continue to emit less visible, smaller particles. Additionally, gasoline engines, particularly of the gasoline direct injection design, emit large numbers of small particles. The regulations known as EURO 5 Reg 83 are being applied to vehicular diesel engine exhaust streams.

Nanoparticles in IC engine exhausts cannot readily be counted using technology such as laser light scattering instruments, which can however be used for larger, micron-sized particles. Instruments known as Condensation Particle Counters ("CPC") are commercially available, which pass the particle-containing gas through a supersaturated vapour, conventionally a vapour of an organic liquid such as iso-propanol or n-butanol, although water vapour has been used, so that the particles act as nuclei for vapour condensation. Accordingly, under suitable conditions, nanoparticles can grow to sizes of up to 10-12 um, and can thus be counted using a conventional scattering technology. A problem with this system, however, is that any type of particle can act as a nucleus, and not just solid carbonaceous or metal oxide particles. This problem is exacerbated at the high dilutions used in the counting technique. IC engine exhausts contain, in addition to the solid carbonaceous or metal oxide particles which are of legislative interest, hydrocarbon and other organic condensed solids and sulphur compounds, and may contain nitrogen oxides, organic acids and phosphoric acid. Each of these components can, under certain conditions act as a nucleus and accordingly confuse the counting process. Some attempts have been made by adjusting conditions in the CPC and by signal processing, to discriminate between true solid particles and pseudo-solid nuclei, but there remains the need for alternative approaches, especially as increasing attention is paid to the potential hazards of nanoparticle emissions.

SAE Paper No 950236 dating from 1995 proposes to measure volatile and solid exhaust particles. The equipment described uses a catalytic stripper which is a section of a diesel exhaust catalyst; a diluted stream of exhaust is passed through the diesel exhaust catalyst before being cooled and being passed to a particle counter such as an electrical aerosol analyzer or a condensation nucleus counter (CNC). An alternate stream of diluted gas is passed to the particle counter without the catalytic stripper treatment, to allow the total, volatile and non-volatile (solid) particle concentrations to be determined. This device is also described in US Patent Application U.S. Pat No. 2004/0139785.

However, the catalytic stripper concept appears to have been abandoned, and the European regulations require only the treatment of the exhaust gas in a heated tube to maintain all volatile components in the vapour phase and air dilution and cooling to avoid nucleation prior to passing the exhaust gas to a CNC for particle counting.

Prof. Nick Collings has recently studied a High Temperature Condensation Particle Counter which potentially avoids the problem of condensing or nucleating volatile material in particle measurement of exhaust gases. See www.cambridgeparticlemeeting.org/sites/default/files/Presentations/2013/NCollings(UofCambridge) 2013 Hot condensation particle counter.pdf The present inventor attempted to solve the problem of analyzing particulates by applying several alternative treatments to an exhaust gas, then passing the treated gas to a particle counter, as described in WO2004/097400 A1, and comparing and reviewing the different results. One of the treatments involved contacting the gas sample with an oxidation catalyst for oxidizing hydrocarbons and a basic material for absorbing acidic species. The preferred catalyst is platinum supported on alumina. The catalyst and absorber are suitably carried on a flow-through ceramic monolith. It is not believed that the apparatus described was ever used commercially in any form. We have now devised a new and improved device, as described below.

There remains, however, the need for a reliable particle counter able to cope with the many different components in exhaust gas streams which can condense or nucleate, directly or indirectly by reaction with other components, to form particles which confuse a CPC or other particle counter instrument. In particular, it would be useful to engineer a system able to be incorporated into portable instruments, such as instruments for road-side testing or on-board test units, and it is believed that the present invention offers such a solution.

The present invention now provides an improved nanoparticle counter instrument, having a gas treatment stage prior to a nanoparticle counter device, in which the gas treatment stage comprises an oxidation catalyst and an absorber effective to absorb gaseous sulphur compounds, desirably nitrogen oxides and other acid vapour species that when cooled could nucleate to form particles, in which the gas treatment stage is supported on a: metal flow-through monolith of no more than 400 cells/sq in and having an open area of not less than 80%, preferably not less than 90% and most desirably not less than 95%. Preferably, the gas treatment stage is contained in a replaceable unit, which may, for example, be disposed of after a pre-determined usage period. Alternatively, the unit may be recycled and/or regenerated.

Although the present invention has been developed primarily with a conventional commercial CPC device, the principles may be used with any particle counter subject to interference from non-solid "particles" especially those derived from combustion gas streams. The present invention may desirably be combined with a high temperature condensation particle counter, which avoids the need for cooling the gas stream leaving the catalyst absorber unit and associated potential particle diffusion losses.

FIG. 1 is a block diagram of a nanoparticle counter instrument according to the invention.

A sampling gas line (1) for particle-containing exhaust gas is led into a gas treatment stage (2) containing a flow-through metal monolith having specified cell count and specified open area and supported on the monolith, an oxidation catalyst and an absorber effective to absorb gaseous sulphur compounds and desirably nitrogen oxides that when cooled could nucleate to form particles. The pretreated gas is then fed to a nanoparticle counter (3).

The gas treatment unit is conveniently but not essentially contained within a single housing. Desirably, the housing is asymmetric, so that in conjunction with fittings, it is capable of being mounted only in the correct manner, that is to say with the catalyst zone upstream. Conventional catalyst structures, such as those using a ceramic or metallic flow-through honeycomb-like substrate structure, may be used in the present invention. Structures that tend to impede the flow of particles are not preferred, since they can distort the particle count results. We believe that a key factor in avoiding impeding the flow of particles is the open area of the monolith. For example, the conventional state of the art ceramic monolith, as used in the WO2004/0907400 disclosure, had a wall thickness of 8 mil (thousands of an inch). We have calculated that, for a 400 cell per sq inch monolith, this would yield an open area of 70.56%. The SAE paper No 950236 uses a catalyst using a 12.2 mil wall thickness ceramic monolith; this would give an open area of 60.8%.

The catalyst may be any catalytically-active substance effective under the operating conditions. Suitably, the catalyst is or comprises a platinum group metal, preferably platinum or palladium, more preferably a palladium/platinum catalyst, although other materials, such as manganese, or other suitable metal compounds, active under the particular conditions to oxidise substantially all of the organic vapours and especially hydrocarbons in the gas passed through the catalyst, may be used. It is not desirable to oxidize $SO_2$ to sulphate species. The extent to which this happens depends on the catalyst formulation and on the operating temperature. With operation at temperatures around 300-350° C. the amount of $SO_2$ oxidation should be small. Any $SO_2$ that is oxidized will be absorbed on the absorber. It is not believed that $SO_2$ itself causes any substantial interference with particle counting.

The catalyst may comprise a single component or may comprise one or more promoters or other active or inert ingredients, including materials which increase the effective surface area of the catalyst or inhibit the oxidation of $SO_2$ to sulphate species.

We have found that having the active catalytic oxidation phase such as platinum supported on a washcoat comprising a silica/alumina rather the conventional and state of the art alumina results in a desirable resistance to catalyst poisoning by sulphur species. Also, that this leads to extended high performance and catalysts longevity.

Such catalysts may be manufactured according to our procedures by the person skilled in the art.

Positioned downstream of the catalyst is an absorber. Suitable absorbers include alkaline earth metal or alkali metal compounds, such as carbonates or oxides of barium, strontium or calcium, or like materials effective to bind sulphate-type species.

Whilst the catalyst and absorber functions may be carried out by separate units mounted within a housing through which the test gas is passed, it is also desirable, in order to minimize particle losses, in a further embodiment to deposit catalyst and absorber coatings sequentially on the same support. Thus, a layer of absorber-containing component may be deposited first on a catalyst support, for example by spraying the catalyst support with or dipping the catalyst support-in a slurry or solution comprising the absorber component or a precursor of the absorber component. Other catalyst coating operations including vacuum coating may be used. The thus-coated support may then be dried and calcined then the process repeated with a slurry or solution containing catalyst components, optionally by reversing the support. In the case of a support monolith, this can thus yield a monolith coated with an upstream catalyst coating and a downstream absorber coating. Other unit designs are available to the skilled person, and zones containing mixtures of catalyst and absorber or an inner layer of oxidation catalyst and an outermost layer of absorber may be advantageous.

Desirably, the total unit of catalyst zone and absorber has a penetration of at least 80% for 10 nm particles (penetration being defined for a particular particle size and specified conditions as 100 times the concentration of particles leaving the unit divided by the concentration of particles entering the unit), more desirably a penetration of at least 90%. Accordingly, it is preferred to use relatively low cell density (no greater than 400 cells per sq in) flowthrough monoliths, with high open facial area as specified above. In general, it is preferred to use shorter catalyst zones in order the minimize particle diffusion losses, providing the zone is sufficient to achieve the desired level of catalytic oxidation. It is to be noted that in the above-mentioned WO2004/0907400 such disclosure as there is relates to a vastly different monolith shape, namely 34 mm diameter by 110 mm length.

A novel monolith particularly suitable for use in the present invention is a metal foil monolith, wherein the foil has a maximum thickness of 50 micron, preferably 20 micron, and a face open area of at least 90%. The clear trend in the catalyst art is to increase cell density in support monoliths; the present invention runs counter to that trend, with a maximum of 400 cells per square inch and preferably no more than 200 cpsi.

The sample gas and the catalyst/absorber unit are both preferably provided with heating means-to ensure that the catalyst is operated at the most advantageous temperature for the catalytic reactions and to ensure the volatile material is all in the vapour phase. This is generally in the range 150 to 550° C., preferably in the range 200 to 375° C. The skilled person will recognize that the sample gas must be preheated to the desired operating temperature before it reaches the monolith, because getting sufficient heat through a monolith, particularly a ceramic monolith, is not possible practically.

It will be realized that, depending on the concentration of non-solid particles in the test gas, and the use that the instrument experiences, the absorber will eventually become saturated, (although desirably it is designed to have an extended operating life) and the catalyst itself may become less effective through poisoning or coking and the absorber may become saturated. It is therefore preferable to replace the catalyst/absorber unit before the unit becomes ineffective. Desirably, therefore, the unit is in the form of a readily replaceable unit mounted in the particle counter instrument. Whilst it is possible to contemplate regeneration of both catalyst and absorber, it is presently preferred to dispose of the unit safely. As mentioned above, it is preferred to use an asymmetric design.

In several of the tests supporting this invention a catalyst/absorber unit was approximately 42 mm long and 19.05 mm diameter (external dimensions); a number of alternatives were also used, for example 38 mm long and 22.2 mm diameter with catalyst lengths of 37 mm and 32 mm respectively. Active oxidation catalyst and absorber loadings within such units may range from 5 g/cubic foot to 200 g/cubic foot and preferably 10 to 100 g/cubic foot if the oxidation catalyst is a precious metal such as Pt, Pd, Rh and/or Au, higher if a base metal derivatives are used eg manganese oxides, and 20 g/cubic foot to 1000 g/cubic foot or more and preferably 50 g/cubic foot to 300 g/cubic foot of the absorber material.

The invention will now be described by way of example. It is to be noted that in this art, it is conventional for Imperial units to be used for certain measurements, rather than SI or metric units.

Gas Treatment Stage Preparation

A cylindrical cordierite monolith with a plurality of square parallel channels (400 per square inch) running along its length (6 inches), with a diameter of 5.66 inches, was dipped into an aqueous dispersion (35% by weight) of a dispersible high surface area silica/alumina containing 30% silica and having a BET surface area of 140 $m^2/g$. The nominal wall thickness was 2.5 mil (thousandth of an inch) and we calculate that this has a 90.2% open area. The dispersion was made by ball milling the silica/alumina with water acidified to about pH=4 with dilute nitric acid. Ball milling was continued until the particle size (d50) was in the range 5-15 microns as measured by a Malvern Instruments Mastersizer 2000. A small amount of dilute ammonia solution was then added gradually with stirring to gel the dispersion to the extent judged to be suitable for coating the monolith.

The monolith was submerged in the dispersion, removed and allowed to drain for a few minutes. Excess dispersion was removed from the monolith by shaking it and then by blowing a stream of high velocity air from an air gun through the channels. The monolith was then dried by passing a flow of hot air (120° C.) through the channels over a period of 3 hours, after which it was fired in static air in an electric furnace programmed to increase the temperature from ambient to 500° C. over 2 hours then to hold that temperature for 2.5 hours, after which it was allowed to cool to room temperature without heating being applied. Comparing the weights of the uncoated monolith with that of the monolith after coating and calcining showed that a washcoat loading of 2.3 grams per cubic inch of the gross monolith volume.

Using a band saw, the washcoated monolith was cut across its diameter into slices each of 38 mm thick. The slices were impregnated by immersion into a solution in a shallow dish to a depth of 25 mm; additional solution was added to maintain the liquid depth as solution was absorbed by the washcoated monolith. The solution contained sufficient tetramminoplatinum dinitrate such that when dried and calcined the impregated monolith-contained 90 g Pt per cubic foot of coated monolith. The impregnating solution also contained a small amount an ethylhyroxycellulose (Natrosol™ Ashland Chemicals) to increase the viscosity of the solution sufficiently to prevent wicking of the solution up the monolith significantly above the level of liquid in the dish. The appropriate concentration of the impregnation solution was determined by estimating the pore volume of the washcoated monolith by the cold water pick-up method. After impregnation, the part-platinized monolith was dried at 120° C. for two hours and then calcined at 500° C. for three hours as described above. When cooled, the part-platinized monolith was turned over and immersed in a 12.5 mm deep solution of barium acetate in a dish. Once more, the viscosity of the solution was controlled using Natrosol™. As before, barium acetate solution was added to maintain the depth as solution was absorbed. After sitting in the solution for a few minutes, the monolith was carefully removed and allowed to drain on a raised wire mesh. The monolith was then dried at 120° C. and calcined at 500° C. as previously described. The loading of barium corresponded to 250 g Ba per cubic foot of monolith. The resulting monolith had two zones along the length of the channels, one platinized 25 mm long and one with barium, 12.5 mm long.

The above procedure was repeated with a metal foil monolith, of 350 cpsi. Metal foil monoliths can generally be made with thinner wall sections than ceramic monoliths, which we believe to be advantageous. An outer stainless steel tube 25.3 mm long, 17.9 mm diameter with 1 mm wall thickness was fitted with an inner structure having 350 cells per sq in and manufactured from a commercial catalyst monolith metal foil of 0.05 mm thickness. This is calculated to have an open area of 91.5%. The unit was cleaned with detergent-containing water then rinsed several times with deionized water before treating with pure acetone and air drying. It was then heated in an electric furnace in an air atmosphere at 550° C. for 3 hours to develop a thin resistant oxide film on the foil surface. The unit was then washcoated three times using the procedure described above, with a dispersion containing 19.5% solids measured after drying and calcinations at 500° C. The final washcoat loading corresponded to 2.0 gram per cubic inch of the overall volume of the unit. The resulting washcoated unit was then platinised along its entire length corresponding to a loading of 90 gram per cubic foot. An exit zone 7.5 mm long was impregnated with strontium acetate so after calcination at 500° C. for two hours, it contained 300 gram per cubic foot of strontium.

The washcoated and zone-impregnated ceramic monolith was then cored with a diamond core drill to produce monoliths 38 mm long and about 16 mm diameter. The cores were then mounted in stainless steel (type 316) mantles of a suitable length (42 mm) and diameter (19 mm) and retained in position by an intumescent mat followed by heat treatment at 450° C. in air for 3 hours in 300 liter per hour of flowing air. Stainless steel inlet and exit cones having central openings with 10 mm diameter tubing were welded to each unit for subsequent testing. Other units were made having different dimensions eg external 22.2 mm and 25.4 mm diameter and 35.5 mm and 31.0 mm long.

Tests

1. Hydrocarbon Removal

In these tests a unit described above (eg OD 19 mm, length 42 mm, not the monolith size) was configured so the sample gas flow first passed over the oxidation part and then the sulphur absorption part. Standard analytical and particle measurement techniques were used, and in all cases HEPA filtered air was used as a source of gas into which hydrocarbon was vapourised using known amounts of the hydrocarbon concerned. Concentrations were checked by chromatographic analysis (FID). The gas containing hydrocarbon was pre-heated to 350° C. and the unit was maintained at the same temperature by an electrical heater and a control device. The exit gas was diluted with heated HEPA filtered air prior to analysis. Condensable hydrocarbons used included decane, hexadecane and toluene. Gas flow rates through the unit were in the range 50 liter per hour to 500 liter per hour and typically 180 liter per hour. Inlet hydrocarbon concentrations were varied between 30 ppm and 1000 ppm and within experimental error no hydrocarbon was detected in the exit gas corresponding to at least 99.8% removal of hydrocarbon. Tetracontain ($C_{40}H_{32}$) a "standard" volatile particulate in automotive measurements was vapourised before entering the unit. Particles in cooled gas were measured using standard procedures with a commercial CPC. With the unit maintained at room temperature the expected number of particles was detected, and as the temperature was increased the number measured decreased to effectively zero at 350° C.

2. Particle Penetration

Penetration of small particles was measured to estimate particle losses taking place mainly by thermophoretic and diffusion processes in a unit equipped with short stainless steel cores and short 10 mm inlet and exit pipes (as described above). Diesel engine exhaust derived particles of known size were passed through the unit at room temperature (to minimize catalytic oxidation) the penetration of 10 nm particles was greater than 80%. Similar results were obtained when metal particles were used at higher temperatures where hydrocarbons would be oxidized. The measured penetration depended on the unit dimensions, flow rates and temperature.

3. Sulphur Tolerance

The exceptional tolerance of the unit towards sulphur poisoning was demonstrated by using test gas containing various amounts of sulphur dioxide with hydrocarbon and air under operating conditions described above over prolonged periods. In one experiment using n-decane the unit was treated with gas containing about 100 ppm sulphur dioxide for 1000 hours and there remained no hydrocarbon detected in the exit gas stream detected by gas chromatography. Particle measurements on the exit gas did not detect particles resulting from nucleation of sulphuric acid, whereas a separate test with a conventional platinum on alumina oxidation catalyst produced sulphuric acid particles of about 12 nm size after being on line for a short time.

1000 hours of sulphur exposure typically would correspond to a particle counting instrument being in use for considerably more than a year.

4. Vehicle Exhaust Gas

Diesel exhaust gas was obtained from a car with a four cylinder diesel engine and tailpipe emissions compliant with Euro 5 standards operating on fuel with less than 10 ppm sulphur and synthetic long-life lubrication oil, having had all of the exhaust gas aftertreatment components removed. The exhaust gas was taken to a constant volume sampling system using filtered air in the standard way. With the engine running at 2500 revs per minute an exhaust gas sample was diluted 10 to 1 with HEPA filtered air and fed through the unit. The exit gas from the unit was taken to a conventional CPC operating with n-butanol and a lower particle size cut-off below 10 nm. The temperature of the unit was initially at ambient temperature and the number of particles counted corresponded to $6 \times 10^7$ to $1 \times 10^8$ particles per cc. The sample gas pre-heater and the heating block containing the unit was then switched on and allowed to increase to a controlled temperature of 350° C. measurements were made an hour later to ensure complete thermal equilibration. The number of particles counted by the CPC had dramatically decreased to effectively zero showing that a very high proportion of the engine-out particles were of a volatile nature.

In another experiment, a four cylinder gasoline engine with a displacement of 1.6 liters in a car compliant to Euro Stage 3 tailpipe emissions standards fueled with regular low sulphur gasoline was used to provide an exhaust gas sample from immediately before the close-coupled three-way catalyst fitted to the engine. Particle measurements were made with a Cambustion DMS500 fast particle analyzer that required a higher flow of test gas than the previously-used CPC. The test gas was diluted 4 fold with HEPA filtered air at the point of sampling, and there was a secondary dilution in the particle counting instrument with a dilution ratio of 20 to 1 typically being used. A very large number of particles were measured corresponding to $3 \times 10^8$ particles per cc whereas after passage through the unit of the invention at 350° C. a much smaller number of solid particles was measured corresponding to less than $5 \times 10^6$ particles per cc. These were thought to have originated mainly from inorganic additives in the lubrication oil.

In laboratory tests, it is usual to use propene as a model gas for diesel exhaust gas. This is used in the tests described below. A unit described above with external dimensions OD 19 mm and length 42 mm was configured in a test unit so the gas flow containing 200, 500 or 1000 ppm propene in air with or without addition of water was first passed over the oxidation part and then the sulphur absorption part. This test was to mimic the behaviour when high levels of hydrocarbon are present in exhaust gas such as when late injection of fuel into an engine takes place during regeneration of a particulate filter and the exhaust gas is not diluted prior to its particulate number content being measured. This might be the case in a portable emissions measurement instrument. The total gas flow was 96 liter/hour with no added water, and 102 liter/hour when added water (6.0%) was present, typical of what might be used in conjunction with a condensation particle counter. When no added water was present in the inlet gas the test began just above room temperature and temperature was gradually increased until no propene was detected in the exit gas stream by a Fourier Transform infrared spectrometer. The same instrument was used to confirm the inlet concentration of propene that was set and maintained by mass flow controllers. When water was added to the inlet gas mixture the temperature was kept above the dew point. The temperature at which no propene was detected in the exit gas was 140° C. when 200 ppm of propene was in the inlet gas, 150° C. when 500 ppm propene was in the inlet gas and 170° C. when 1000 ppm propene was in the inlet gas. Addition of water (6.0%) in the inlet gas caused an increase of about 5° C. in each of these temperatures. Tests with the smaller 25.3 mm long and 17.9 mm diameter outside dimensions metal foil unit with high open frontal area similarly configured in the test equipment gave similar results with complete propene removal at 145° C., 155° C. and 177° C. respectively confirming that when operated at temperatures above 250° C., and particularly above 300° C. all hydrocarbons in the vapour phase will be oxidised by either unit and so prevent hydrocarbon nucleation.

The invention claimed is:

1. An improved nanoparticle counter instrument having a gas treatment stage prior to a nanoparticle counter device,
    the gas treatment stage comprises an oxidation catalyst or oxidizing condensable hydrocarbons and an absorber effective to absorb gaseous sulfur compounds and desirably nitrogen oxides that when cooled could nucleate to form particles, and
    the gas treatment stage is supported on a metal foil through-flow monolith having no more than 400 cells per square inch and a foil thickness of no more than 50 microns, having an open area of at least 90%, having sequential axial loadings of the catalyst and the absorber, and exhibiting a penetration for 10 nm particles of at least 80% at room temperature (defined by a concentration of particles leaving the gas treatment stage divided by a concentration of particles entering the gas treatment stage x 100).

2. An instrument as claimed in claim 1, wherein the monolith foil thickness is no more than 20 microns.

3. An instrument as claimed in claim 1, wherein the gas treatment stage comprises a catalyst selected from platinum, palladium, rhodium, gold and mixtures thereof.

4. An instrument as claimed in claim 1, wherein the gas treatment stage comprises an absorber selected from alkali metal compounds and alkaline earth metal compounds.

5. An instrument as claimed in claim 1, wherein the gas treatment stage includes a downstream zone in which catalyst and absorber are mixed.

6. An instrument as claimed in claim 1, wherein the gas treatment stage includes a zone having an inner layer of oxidation catalyst and an outermost layer of absorber.

7. A method of counting solid nanoparticles in an exhaust gas stream using a particle counter instrument, comprising a gas treatment step, comprising oxidizing volatile organic materials then subsequently absorbing sulfur materials from the gas phase, using a unit as claimed in claim 1.

8. An instrument as claimed in claim 1, wherein the metal foil comprises an oxide film on its surface and a washcoat comprising silica/alumina, the oxidation catalyst and the absorber are supported on the washcoat.

9. An instrument as claimed in claim 8, wherein the silica forms 5 to 50% of the silica/alumina, by weight.

10. An instrument as claimed in claim 9, wherein the oxidation catalyst is selected from platinum, palladium, rhodium and gold and mixtures thereof.

11. An instrument as claimed in claim 10, wherein the absorber is selected from barium compounds, strontium compounds and calcium compounds.

12. An instrument as claimed in claim 11, wherein the gas treatment stage includes a zone having an inner layer of the oxidation catalyst and an outermost layer of the absorber.

* * * * *